United States Patent [19]

Nemcek et al.

[11] Patent Number: 4,563,486

[45] Date of Patent: Jan. 7, 1986

[54] POLYMERIZABLE COMPOSITION COMPRISING (A) PHOSPHORUS OXYACID (B) AMINE AND (C) INORGANIC MATERIAL

[75] Inventors: Jozef Nemcek, Chester; Thomas A. Roberts, Cheshire, both of England

[73] Assignee: Imperial Chemical Industries PLC, London, England

[21] Appl. No.: 620,920

[22] Filed: Jun. 15, 1984

[30] Foreign Application Priority Data

Jun. 16, 1983 [GB] United Kingdom ............... 8316445

[51] Int. Cl.$^4$ ............... C08K 3/34; C08F 230/02; A61K 5/06
[52] U.S. Cl. ............... 523/115; 523/116; 524/789; 524/850; 524/852
[58] Field of Search ............... 524/850, 789; 523/115, 523/116; 204/159.23; 526/277, 310, 312, 193

[56] References Cited

U.S. PATENT DOCUMENTS

| | | | |
|---|---|---|---|
| 3,956,421 | 5/1976 | Roberts et al. | 526/277 |
| 3,963,512 | 6/1976 | Swift et al. | 524/850 |
| 4,222,780 | 9/1980 | Shibatani et al. | 526/277 |
| 4,259,117 | 3/1981 | Yamauchi et al. | 526/277 |
| 4,374,937 | 2/1983 | Nemcek et al. | 204/159.23 |
| 4,407,984 | 10/1983 | Ratcliffe et al. | 523/115 |
| 4,439,380 | 3/1984 | Michl et al. | 264/16 |
| 4,442,239 | 4/1984 | Tsunekawa et al. | 525/116 |

FOREIGN PATENT DOCUMENTS 7107703 2/1971 Japan ............... 526/277

OTHER PUBLICATIONS

*Chemical Abstracts*, 1980, vol. 93(b), p. 467, No. 54013v.
C.A. 89–46097 (1978) Mead et al, Texas Inst.
C.A. 76–113899 (1972) Kosugi et al, JP71–40686.

*Primary Examiner*—Herbert J. Lilling
*Attorney, Agent, or Firm*—Cushman, Darby & Cushman

[57] ABSTRACT

A polymerizable composition is formed from (a) a polymerizable olefinically unsaturated substance, (b) a phosphorus oxyacid and an organic amine, at least one of which bears a polymerizable olefinically unsaturated group and optionally (c) a particulate inorganic material. Such compositions are useful in dental applications.

6 Claims, No Drawings

POLYMERIZABLE COMPOSITION COMPRISING (A) PHOSPHORUS OXYACID (B) AMINE AND (C) INORGANIC MATERIAL

This invention relates to polymerisable compositions.

We have found that where an organic medium which comprises a polymerisable olefinically unsaturated substance is polymerised in contact with the surface of an inorganic material bonding of the polymerised organic medium to the surface may be improved by incorporating in the organic medium certain phosphorus oxyacids and certain amines as hereinafter defined. The inorganic material may be in the form of a coherent mass or a particulate material. Where the inorganic material is in particulate form and is suspended or dispersed in the organic medium the mechanical and physical properties, e.g. solvent resistance, of cured products prepared from such compositions are often better than those of similar composition described in European Patent Specification No. 0013491B.

Accordingly, the present invention provides a polymerisable composition comprising:
(a) an organic medium which comprises a polymerisable olefinically unsaturated substance which bears one or more polymerisable olefinically unsaturated groups;
(b) a phosphorus oxyacid having the formula:

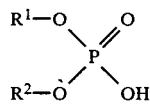

wherein
$R^1$ is a hydrocarbyl group or a polyether or polyester chain,
$R^2$ is hydrogen or a hydrocarbyl group or a polyether or polyester chain; and
(c) an organic amine having the formula:

wherein
$R^3$ is a hydrocarbyl group or a polyether or polyester chain, and
$R^4$ and $R^5$, which may be the same or different, are hydrogen, hydrocarbyl or polyether or polyester chains,
except that at least one of the groups $R^1$, $R^2$, $R^3$, $R^4$ and $R^5$ comprises a polymerisable olefinically unsaturated group.

As examples of polymerisable olefinically unsaturated substances of which polymerisable compositions according to the present invention are comprised and which contain one polymerisable olefinically unsaturated group may be mentioned readily available monomers selected from the classes including inter alia hydrocarbons, e.g. styrene; ethers, e.g. vinyl ethyl ether; esters, e.g. vinyl acetate, methyl methacrylate, ethyl acrylate, butyl methacrylate and 2-ethyhexyl methacrylate; and amides, e.g. N-vinyl pyrrolidone, and N-alkyl acrylamide.

As examples of polymerisable olefinically unsaturated substances of which polymerisable compositions according to the present invention are comprised and which contain a plurality of polymerisable olefinically unsaturated groups may be mentioned inter alia the poly(alk)acrylate esters of, for example, diethylene glycol, trimethylolpropane and pentaerythritol, e.g. diethylene glycol dimethacrylate.

Preferably polymerisable olefinically unsaturated substances of which polymerisable compositions according to the present invention are comprised are polymerisable prepolymers. As examples of such prepolymers may be mentioned vinyl urethanes, for example those described in United Kingdom Patent Specification Nos. 1,352,063, 1,465,097 and 1,498,421 and German Offenlegunsschrift No. 2,419,887; the reaction products of a diol, particularly a bisphenol, with a glycidyl alkacrylate, for example those described in U.S. patent specification Nos. 3066112 and 4131729; and the reaction products of an aromatic compound, formaldehyde and a polymerisable olefinically unsaturated carboxylic acid as described in our European patent application No. 83307128. The disclosures in the aforementioned specifications and application are incorporated herein by way of reference.

Preferably the aforesaid polymerisable prepolymers are selected from the group consisting of vinyl urethanes as hereinbefore described which are the reaction products of a urethane prepolymer and a hydroxyalkyl ester of acrylic or methacrylic acid, the urethane prepolymer being the reaction product of a di-isocyanate of the structure OCN-$R^6$-NCO, where $R^6$ is a divalent hydrocarbyl radical, preferably an alkylene radical having up to ten carbon atoms, e.g. hexamethylene, and a diol of the structure HO-$R^7$-OH, where $R^7$ is the residue of a condensate of an alkylene oxide with an organic compound containing two phenolic or alcoholic groups; the aforesaid reaction products described in European patent application No. 83307128; and the reaction product of a glycidyl alkacrylate and a diol of the formula:

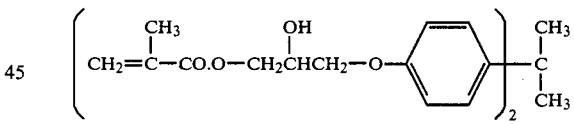

which polymerisable prepolymers are optionally in admixture with a polymerisable olefinically unsaturated monomer having one or more polymerisable olefinically unsaturated groups formed by esterifying acrylic or methacrylic acid with a hydroxy compound or a polyol, preferably a diol, e.g. triethylene glycol dimethacrylate.

Where a group $R^1$, $R^2$, $R^3$, $R^4$ or $R^5$ in phosphorus oxyacids and organic amines of which polymerisable compositions according to the present invention are comprised is a hydrocarbyl group it may be an alkyl, e.g. octyl; aralkyl, e.g. benzyl; alkaryl, e.g. tolyl; or aryl, e.g. phenyl, group.

The groups $R^1$, $R^2$, $R^3$, $R^4$ and $R^5$ may carry substituents, which may be in-chain or pendant, which do not interact unduly adversely with the aforesaid surface of the inorganic solid nor unduly adversely affect the polymerisation of the polymerisable composition. As examples of such suitable substituents may be mentioned ester, hydroxy, halogen and ether groups.

Preferably both the phosphorus oxyacid and the organic amine are polymerisable olefinically unsaturated compounds since use of such a mixture further improves the adhesion of the polymer prepared by polymerisation of the polymerisable compositions to the aforesaid surface of the inorganic material.

Preferably at least one of the groups $R^1$, $R^2$, $R^3$, $R^4$ and $R^5$ and particularly preferably at least one of the groups $R^1$ and $R^2$ and at least one of the groups $R^3$, $R^4$ and $R^5$ is, or is derived from, a hydrocarbyl group having at least six carbon atoms or a polyether, e.g. polypropylene oxide, or polyester chain, e.g. polycaprolactone of molecular weight greater than 200 and more particularly preferably is, or is derived from, a long chain alkyl group containing 8 to 22 carbon atoms or a polyether or polyester chain of molecular weight between 300 and 10,000. Use of a mixture of phosphorous oxyacid and organic amine wherein the groups $R^1$, $R^2$, $R^3$, $R^4$ and $R^5$ are selected from these preferred definitions allows a greater concentration of particulate inorganic material to be dispersed in the organic medium and/or affords a decrease in the viscosity of the dispersion.

As examples of polymerisable olefinically unsaturated groups which may be present in a phosphorus oxyacid or an organic amine of which polymerisable compositions according to the present invention are comprised may be mentioned inter alia (alk)-acryloxyalkyl, and (alk)-acroylamidoalkyl, e.g. methacryloxypropyl, and acrylamidobutyl; allyl; residues of naturally occurring unsaturated acids, e.g. oleic acid; $CH_2=CH(CH_2)_m-$, where m is 6 to 50 e.g. undecenyl; $CH_2=CH-Ar-(CH_2)_n-$, where n is 6 to 50, $CH_2=CR^8COO(CH_2)_p-$, where R is hydrogen, methyl or ethyl and p is 6 to 50; and polybutadiene. It is often preferred that the polymerisable olefinically unsaturated group is distant the nitrogen or phosphorus atom.

Whilst we do not exclude the possibility that phosphorus oxyacids of which polymerisable compositions according to the present invention are comprised may be in the form of a mono-ester or a mixture of mono- and di-esters, it is often preferred that a diester is present, preferably a diester in which both ester groups, which may be the same or different, contain a polymerisable olefinically unsaturated group. Conveniently, a mixture of phosphorous oxyacids may be used, typically a mixture of mono- and di-esters.

As specific examples of phosphorus oxyacids of which polymerisable compositions according to the present invention may be comprised may be mentioned methacroyloxypropyl phosphate, di(methacroyloxypropyl) phosphate, oleyl dihydrogen phosphate, dioleyl hydrogen phosphate, di(undecenyl) phosphate, methacroyloxyhexyl phosphate, acroyloxypolypropoxyl phosphate, cholesteryl phosphate, and methacroyloxydodecyl phosphate.

Whilst we do not exclude the possibility that organic amines of which polymerisable compositions according to the present invention are comprised may be primary amines, i.e. $R^3$ and $R^4$ are hydrogen, or secondary amines, i.e. $R^3$ is hydrogen, preferably they are tertiary amines and more preferably each of the three substituent groups on the nitrogen contains polymerisable olefinically unsaturated group, which groups may be the same or different.

As specific examples of organic amines of which polymerisable compositions according to the present invention may be comprised may be mentioned methacroyloxyethyl diethyl amine, di(methacroyloxyethyl) methylamine, olylamine, undecenylamine, methacroyloxypolypropoxyl amine, cholesterylamine, methacroyloxypropyl dimethylamine, tri(methacroylpolyoxypropyl)amine, dodecyl di(methacroyloxyethyl)amine.

The organic medium used in a polymerisable composition according to the present invention should not contain acidic or basic groups.

Polymerisable compositions according to the present invention may be used in the form of thin films. For example, they may be used for coating a substantially inorganic surface, e.g. as a corrosion resistant coating on a metal or as a glaze for teeth; or they may be used as adhesives, e.g. to bond a dental filling or cap into or onto a tooth cavity.

However, in a preferred embodiment of the present invention the polymerisable composition as hereinbefore defined is in intimate admixture with a particulate inorganic material. Such compositions may be converted into substantially three-dimensional articles and objects or into coatings or films.

A particulate inorganic material of which a polymerisable composition according to the present invention may be comprised may be any conventional particulate filler material, for example, metal oxides, e.g. alumina, titanium dioxide, magnetic iron oxide; carbon black; graphite; inorganic salts, e.g. hydroxy apatite; metals; clay and preferably is a siliceous material, for example silica and silicate-based glasses.

Where a particulate inorganic material is present in a polymerisable composition according to the present invention and where it is a siliceous particulate material it may be, for example, a silicate salt, e.g. aluminium silicate or calcium silicate, or a silicate-containing mineral in finely divided form, e.g. talc, or preferably silica or a silicate based glass. Silica may be, for example, comminuted crystalline silica, e.g. sand, or preferably a colloidal silica, e.g. a pyrogenic or fumed silica, having particles of submicron dimensions. The silicate-based glass may be, for example, a borosilicate, which may contain small amounts of other so-called glass modifying oxides, e.g. barium oxide and strontium oxide.

The particulate inorganic material may, for example, be in the form of spheres, platelets, fibres, whiskers or it may be irregularly shaped.

It is preferred that at least 50% of the particles in the particulate inorganic material should have a maximum dimension of not greater than 50 microns. By this is meant that the maximum dimension of the particles in any direction should not be greater than 50 microns. Thus, where the particulate inorganic material is in the form of spheres at least 50% of the spheres should have a diameter of not greater than 500 microns. Where the particulate inorganic material is in the form of fibres at least 50% of the fibres should have a length of not greater than 50 microns. Preferably substantially all of the particles in the particulate inorganic material have a maximum dimension of not greater than 50 microns.

A polymerisable composition according to the present invention may comprise large quantities, for example up to 30–50% by volume and sometimes up to 90% by volume, of a particulate inorganic material dispersed in the organic medium. Preferably a polymerisable composition according to the present invention comprises 20–70% by volume of a particulate inorganic material.

Where a polymerisable composition according to the present invention comprises a particulate inorganic material moulded or cast articles for example, sheet, films, rods, tubes and especially articles moulded or cast into a variety of shapes having a specific utility for example handles, knobs, wheels, lids, sanitary ware, etc. or rubbery products e.g. tyres, shoe-soles, gloves may conveniently and advantageously be made from the aforesaid compositions. The particulate inorganic material often provides the finished article with a useful reinforcing, hardening or decorative effect or an increased resistance to solvent attack, or useful electrical properties.

The concentrations of phosphorus oxyacid and organic amine in polymerisable compositions according to the present invention are not critical. For example, we have found that, where the polymerisable composition comprises a particulate inorganic material, noticeable results are obtainable when together they provide from 0.1% by weight and in general there is no further improvement above about 15% by weight relative to the weight of the particulate inorganic material. Typically about 5% by weight of the phosphorus oxyacid and the organic amine together relative to the weight of the particulate inorganic material is used.

The molar ratio of phosphorus oxyacid to organic amine is typically between 0.5:1 to 100:1 and preferably from 1:1 to 3:1.

Preferably the organic medium is liquid at ambient temperatures because dispersion of the particulate inorganic material, where it is used, is more easily effected if no heating is required for liquifaction of the organic medium. However, we do not exclude the possibility that the organic medium may be a solid or semi-solid at ambient temperatures, the polymerisable composition may then be prepared at an elevated temperature above the melting point or softening point of the medium, which temperature should be below 250° C. and preferably below 150° C.

Polymerisation of polymerisable compositions according to the present invention may be initiated by a suitable free radical initiator system. Such initiator systems include azo systems, organic peroxides or preferably photo-initiator systems as described in United Kingdom Patent Specification No. 1408265 and European Patent Publication No. 59649A, the disclosures of which are incorporated herein be way of reference.

Polymerisable compositions according to the present invention which contain a photo-initiating system, preferably a photo-initiating system which is activated by visible radiation, are particularly useful as dental compositions.

Accordingly, a further aspect of the present invention provides a dental composition which comprises (a) a polymerisable prepolymer comprising a plurality of polymerisable olefinically unsaturated groups and being the reaction product of (i) a urethane and an olefinically unsaturated monomer reactive with the urethane or (ii) an aromatic compound, formaldehyde and an olefinically unsaturated carboxylic acid, (b) a phosphorus oxyacid as hereinbefore defined, (c) an organic amine as hereinbefore defined, (d) a free radical initiator system, preferably a photo-initiator system and optionally (e) a particulate inorganic material.

Where a dental composition according to the present invention comprises a particulate inorganic material is is preferably a siliceous material as hereinbefore defined.

It will be appreciated that a dental composition according to the present invention, where it contains a particulate siliceous material, has sufficient mobility that it may be readily moulded at ambient temperature, for example, by moulding under hand pressure. Conveniently, it will have a paste-like consistency.

A dental composition according to the present invention where it comprises a particulate siliceous material may be applied to the tooth, e.g. as a filling to a cavity in the tooth, and may be polymerised so that the composition is formed into hard material.

An dental composition according to the present invention which does not comprise a particulate inorganic material may be used as a dental glaze or adhesive.

Where a polymerisable prepolymer of which a dental composition according to the present invention is comprised is a solid or semi-solid it is often necessary (in order to produce a dental composition which is fluid) to add to the composition sufficient of a liquid ethylenically unsaturated monomer copolymerisable with the polymerisable prepolymer to make the composition fluid, and in particular, where the composition comprises a particulate siliceous material, to give the composition a paste-like consistency. If desired, the composition may include a liquid copolymerisable ethylenically unsaturated monomer even where the polymerisable prepolymer is itself a liquid.

The amount of such ethylenically unsaturated monomer used may desirably be just sufficient to achieve the desired fluidity in the dental composition. As the use of such amonomer may lead to a reduction in the strength of the dental filling made from the composition it is preferred to use in the composition not more than 100% of ethylenically unsaturated monomer by weight of polymerisable prepolymer, and more preferably not more than 50% by weight.

Suitable liquid copolymerisable ethylenically unsaturated monomers, the polymers of which should be water insoluble, include vinyl monomers, e.g. esters of acrylic and methacrylic acids. Polyfunctional vinyl monomers, that is, monomers containing two or more vinyl groups are also suitable. Suitable monomers include, for example, glycol dimethacrylate, and triethylene glycol diacrylate. The monomers should be of low toxicity.

In order that the cured dental composition should possess higher strength and modulus it is preferred that the polymerisable prepolymer possesses at least one cyclic group. It is preferred that the polymerisable prepolymers possess at least one cyclic group in the chain between the ethylenically unsaturated groups.

Where dental compositions according to the present invention comprise a particulate siliceous material which is in the form of spheres, platelets or is irregularly shaped the maximum dimension of the particles in the particulate siliceous material is preferably not greater than 50 microns, and particularly preferably is not greater than 5 microns.

A photo-initiator system for use in a dental composition according to the present invention preferably comprises at least one photo-sensitiser selected from fluorenone, substituted derivatives thereof, camphorquinone and α-diketones having the structure:

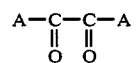

in which the groups A, which may be the same or different, are hydrocarbyl groups or substituted hydrocarbyl groups; and at least one reducing agent capable of reducing the photosensitiser when the photo-sensitiser is in an excited state, e.g. an amine. Preferably an organic peroxy compound, e.g. an organic peroxide, a peracid ester, or a hydroperoxide, is used in admixture with the photo-initiator system.

The dental compositions of the present invention may be cured by irradiating the composition with ultra-violet radiation, that is, with radiation having a wavelength in the range about 230 m$\mu$ up to 400 m$\mu$. The compositions may also be, and preferably are, cured by irradiating with visible radiation and especially with visible radiation having a wavelength in the range 400 m$\mu$ to 500 m$\mu$. Alternatively, a mixture of ultraviolet and visible radiation may be used.

Suitably the concentration of the photosensitiser is 0.001% to 10% by weight, preferably 0.1% to 5% by weight and the concentration of reducing agent is 0.25% to 5% by weight preferably 0.25% to 0.75% by weight, all these percentages being by weight of the polymerisable material in the dental composition.

Mixing of the polymerisable prepolymer with the particulate siliceous material to form a dental composition may be effected by stirring, or shearing, e.g. ball-milling together, the prepolymer and the filler. However, as the polymerisable prepolymer, optionally together with a copolymerisable monomer, may be viscous and thus difficult to stir with the particulate siliceous material so as to achieve adequate mixing the polymerisable prepolymer, optionally together with copolymerisable monomer, may conveniently be diluted with a suitable diluent so as to reduce the viscosity thus enabling adequate mixing of the particulate silicous material to be more readily achieved. When mixing has been effected the diluent may be removed, e.g. by evaporation. Suitably, the diluent may be a copolymerisable ethylenically unsaturated monomer, the concentration of the monomer subsequently being reduced to the desired extent.

In order that a dental composition may be produced in which the particulate siliceous material in the composition adheres particularly well to the cured polymerisable prepolymer it is preferred that the particulate siliceous material be added to the mixture of polymerisable prepolymer, phosphorus oxyacid and organic amine.

In order that a dental base and/or artificial tooth prepared from a dental composition according to the present invention may have flesh coloured and/or natural appearance, it may include small quantities of pigments, opalescent agents and the like.

The dental compositions of the present invention may be used for a range of dental applications. For example, they may be used as filling materials (posterior and anterior), or for the preparation of individual artificial teeth.

The dental composition of the present invention may conveniently be packed in small containers (e.g. 1 g capacity) so as to facilitate handling in the surgery and reduce the risk of inadvertent curing by stray light.

The invention is illustrated by the following Examples.

EXAMPLES 1–3

Dispersions of hydrophilic silica (Aerosil A130; "Aerosil" is a Registered Trade Mark of Degussa), 22% by weight, in methyl methacrylate containing a variety of dispersing agents were prepared by the procedure described in Example 1 of European Patent Specification No. 13491B and cured by the procedure described in Example 19 of the aforementioned specification.

Various physical properties of the cured composites were measured. The results are shown in Table 1.

TABLE 1

| Example No. | Organic Amine | Phosphorus Acid | Flexural Strength MN/m$^2$ | Flexural Modulus GN/m$^2$ | Impact Strength Kg/cm$^2$ |
| --- | --- | --- | --- | --- | --- |
| 1 | A | C | 64 | 3.7 | 4.2 |
| 2 | A | D | 76 | 4.2 | 5.0 |
| 3 | B | D | 73 | 4.0 | 4.7 |
| C.T. | E | C | 60 | 3.7 | 2.5 |

A is C$_{12}$H$_{25}$N(CH$_2$CH$_2$OH)CH$_2$CH$_2$OOCCCH$_3$=CH$_2$.
B is C$_{12}$H$_{25}$N(CH$_2$CH$_2$OH)CH$_2$CH$_2$OOCCH=CH$_2$.
C is di(2-ethylhexyl)phosphoric acid.
D is a 1:1 molar ratio mixture of the mono and diester obtained from the reaction of hydroxypropyl methacylate with phosphorus pentoxide.
E is 90% octadecylamine (Armeen 18, ex AKZO).
C.T is a comparative test.

From the Table it can be seen that where the phosphorous oxyacid does not bear any polymerisable olefinically unsaturated groups use of an organic amine bearing a polymerisable olefinically unsaturated group (Example 1) produces better mechanical properties than use of an organic amine which does not bear a polymerisable olefinically unsaturated group (comparative test) and that where both the phosphorous oxyacid and the organic amine are polymerisable olefinically unsaturated compounds (Examples 2 and 3) further increases in mechanical properties are obtained.

EXAMPLES 4–8

Condensate (32.2 grams; 0.1 mole) obtained by reacting 2,2-bis-(4-hydroxyphenyl) propane and propylene oxide in a molar ratio of 1:2(oxypropylated bisphenol A) was dissolved in approximately 100 grams of methylene dichloride and the resulting solution was added dropwise to a solution of hexamethylene diisocyanate 33.6 g (0.2 mole) in methylene dichloride (100 g) under an atmosphere of nitrogen gas. 4 drops of dibutyl tin dilaurate (available as "Mellite" 12, "Mellite" is a registered trade mark) were added as catalyst. The mixture was stirred under nitrogen for 1 hour after which it was heated under reflux conditions for 9 hours. The mixture was then cooled and a solution of hydroxypropyl methacrylate 29 g (0.2 mole) in methylene dichloride (100 g) was added after which the mixture was heated under reflux conditions for 3 hours. The hydroxypropyl ester comprised isomers in weight ration 2-hydroxypropyl (2.6 parts) to 1-methyl-2-hydroxyethyl (1 part). To the mixture of vinyl urethane (polymerisable prepolymer) and methylene chloride was added triethylene glycol dimethacrylate sufficient to produce polymerisable material containing 50% by weight vinyl urethane and 50% by weight of triethylene glycol dimethacrylate. The methylene chloride was removed by distillation.

A photosensitive catalyst system comprising camphorquinone, and dimethylaminoethyl methacrylate was prepared by dissolving the components in methylene chloride. The solution was added to the polymerisable material; this and subsequent steps being carried out under sodium discharge light.

The camphorquinone concentration was 0.75%, and the dimethylaminoethyl methacrylate concentration was 0.5% by weight based on polymerisable material.

A phosphorus oxyacid and an organic amine followed by a particulate inorganic material were added to the polymerisable composition and photosensitive catalyst system. The mixture was milled on a twin-roll mill operating at ambient temperature under reduced pressure.

Samples of the products from the twin-roll mill were placed in moulds (25 mm×2 mm×2 mm) and cured by exposure for 60 seconds to light of intensity 110–1200 Wm$^{-2}$ measured at 470 m$\mu$. The cured samples were aged for 24 hours at 37° C. and then their flexural properties were determined in a three-point bend test with the supports 20 mm apart and a cross-head speed of 1.0±0.05 mm/min.

Details of the polymerisable compositions and the flexural properties of the products are given in Table 2.

TABLE 2

| | Polymerisable Composition | | | Properties of Product | |
| | Particulate | | | | |
| Example No. | Inorganic Material (%)$^a$ | Phosphorus Oxyacid (%)$^b$ | Organic Amine (%)$^b$ | Flexural Modulus (GPa) | Flexural Strength (MPa) |
|---|---|---|---|---|---|
| 4 | F(43) | J(1.45) | P(1.17) | 7.79 | 84.5 |
| C.T./4 | F(43) | K(1.33) | P(1.17) | 7.08 | 63.2 |
| 5 | G(50) | L(1.64) | P(1.17) | 8.77 | 56.3 |
| C.T./5 | G(50) | K(1.33) | P(1.17) | 7.10 | 47.5 |
| 6 | H(50) | M(3.20) | P(1.17) | 5.78 | 39.0 |
| C.T./6 | H(50) | K(1.33) | P(1.17) | 5.19 | 37.8 |
| 7 | I(50) | K(1.33) | Q(4.8) | 2.78 | 20.2 |
| 8 | I(50) | N(1.0) | Q(4.8) | 4.17 | 28.4 |

F: Fumed Silica (Grade OX50 ex Degussa).
G: Borosilicate glass (2–20 microns).
H: A barium containing glass (Raysorb T-3000).
I: Hydroxy-apatite.
J: A phosphorus oxyacid derived from 1,6-dihydroxyhexane and methacrylic acid.
K: Di-2-ethylhexyl phosphoric acid.
L: A phosphorus oxyacid derived from triethylene glycol and methacrylic acid.
M: A phosphorus oxyacid derived from polypropylene glycol (MW 400) and methacrylic acid.
N: Undecenyl phosphate.
P: A mixture of $C_{12}H_{25}$, $C_{13}H_{29}$ and $C_{14}H_{29}NMe_2$ (ex Albright and Wilson)
Q: $CH_2\!=\!CCH_3CO_2(CHCH_3CH_2O)_nCH_2CH_2N(CH_3)_2$ where n is about 14.
$^a$Percentage by volume of polymerisable composition.
$^b$Percentage by weight based on the weight of particulate inorganic material.
CT/4, CT/5 and CT/6 are comparative tests.

The phosphorus oxyacids designated J, L, and M in Table 2 were prepared as follows. A solution of methacroyl chloride (0.66 moles) in methylene chloride (100 grams) was added dropwise over 30 minutes to a solution of the apropriate diol (0.66 moles) and pyridine (0.73 moles) in methylene chloride (200 grams.) The reaction mixture was stirred at room temperature for 2 hours and then refluxed for 3 hours. The reaction mixture was washed with dilute HCl solution, pyridine chloride was removed by filtration and the filtrate was washed with aqueous sodium bicarbonate solution. Phosphorus pentoxide (0.44 moles) was then added to the filtrate with stirring over 1 hour and the reaction mixture was refluxed for 3 hours. It was washed with aqueous sodium bicarbonate solution, then with water, filtered and the solvent was removed on a rotary evaporator.

The organic amine designated Q in Table 2 was prepared by reacting N,N-dimethylaminoethylpolypropylene glycol in an inert solvent with a small molar excess of pyridine and a small molar excess of methacroyl chloride.

We claim:
1. A polymerisable composition comprising
   (a) an organic medium which comprises a polymerisable olefinically unsaturated substance which bears one or more polymerisable olefinically unsaturated groups;
   (b) a phosphorous oxyacid having the formula:

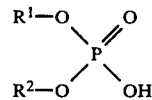

wherein
      $R^1$ is a hydrocarbyl group or a polyether or polyester chain; and
      $R^2$ is hydrogen or a hydrocarbyl group or a polyether or polyester chain; and
   (c) an organic amine having the formula:

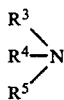

wherein
      $R^3$ is a hydrocarbyl group or a polyether or polyester chain, and
      $R^4$ and $R^5$, which may be the same or different are hydrogen, hydrocarbyl or polyether or polyester chains,
   except that
      (i) at least one of the groups $R^1$, $R^2$, $R^3$, $R^4$ and $R^5$ comprises a polymerisable olefinically unsaturated group
      (ii) at least one of the groups $R^1$ and $R^2$ and at least one of the groups $R^3$, $R^4$ and $R^5$ is, or is derived from, a long chain alkyl group containing 8 to 22 carbon atoms or a polyether or polyester chain of molecular weight between 300 and 10,000; and
   (d) a particulate inorganic material which is dispersed in the mixture of said organic medium, said phosphorus oxyacid and said organic amine; and
   wherein the ratio of said phosphorus oxyacid to said organic amine is in the range from 0.5:1 to 100:1.

2. A polymerisable composition as claimed in claim 1 in which the particulate inorganic material is a siliceous material.

3. A polymerisable composition as claimed in claim 2 in which the siliceous material is a silicate based glass or a silica.

4. A polymerisable composition as claimed in claim 1 wherein the particulate inorganic material provides 20–70% by volume of the polymerisable composition.

5. A dental composition comprising a polymerisable composition as claimed in claim 1, free-radical initiating system, and optionally a particulate inorganic material.

6. A dental composition as claimed in claim 4 wherein the free-radical initiating system is a photo-initiator system.

* * * * *